United States Patent [19]

Alferness

[11] 4,349,015
[45] Sep. 14, 1982

[54] MANUALLY-ACTUABLE CPR APPARATUS

[75] Inventor: Clifton A. Alferness, Woodinville, Wash.

[73] Assignee: Physio-Control Corporation, Redmond, Wash.

[21] Appl. No.: 206,576

[22] Filed: Nov. 14, 1980

[51] Int. Cl.$^3$ ............................................. A61H 31/00
[52] U.S. Cl. ..................................... 128/28; 128/30.2; 128/205.16; 128/205.17
[58] Field of Search ....................... 128/205.13, 205.16, 128/205.17, 28, 205.24, 914, 205.11, 30.2; 434/265

[56] References Cited

U.S. PATENT DOCUMENTS

| | | | |
|---|---|---|---|
| 2,699,163 | 1/1955 | Engstrom | 128/30.2 |
| 3,254,645 | 6/1966 | Rand et al. | 128/52 |
| 3,348,536 | 10/1967 | Tambascia | 128/53 |
| 3,552,390 | 1/1971 | Muller | 128/52 |
| 3,882,860 | 5/1975 | Frimberger | 128/205.13 |
| 4,192,301 | 3/1980 | Hardwick | 128/205.17 |

FOREIGN PATENT DOCUMENTS

| | | | |
|---|---|---|---|
| 238278 | 9/1911 | Fed. Rep. of Germany | 128/28 |
| 762285 | 4/1934 | France | 128/28 |
| 537655 | 6/1956 | Italy | 128/28 |
| 9790 | of 1913 | United Kingdom | 128/28 |

OTHER PUBLICATIONS

M. T. Rudikoff et al., "Mechanisms of Blood Flow During Cardiopulmonary Resuscitation," *Circulation*, Feb. 1980, vol. 61, No. 2, pp. 345-352.

Primary Examiner—Henry J. Recla
Attorney, Agent, or Firm—Christensen, O'Connor, Johnson & Kindness

[57] ABSTRACT

A bellows 10 is adapted to be placed on the chest of a patient and includes a closed chamber which is coupled by a conduit 20 and a first valve apparatus 22 to an airway apparatus 24 adapted to be inserted into the patient's airway, and by a second valve apparatus 26 and a conduit 28 to an inflatable bladder 30 forming part of an abdominal restraint 32 adapted to be secured about that portion of the patient's body in the region of the abdomen. As the bellows is being compressed by the application of manual force, valve apparatus 22 functions to couple the gas being expelled from the bellows into the patient's lungs via airway apparatus 24 (with valve apparatus 22 also functioning to limit the resultant lung pressure to a desired value), whereby the patient's intrathoracic pressure is increased due to the combination of the manual force applied to the patient's chest through the bellows and the pressure generated in the patient's lungs. When the bellows is being decompressed following removal of manual force therefrom, valve apparatus 22 functions to couple gas from the patient's lungs and from the atmosphere back to the bellows. Intrathoracic pressure may be further increased by the use of the abdominal restraint, with valve apparatus 26 functioning to pressurize the inflatable bladder whenever the bellows is compressed and also being selectively actuable (by a pushbutton actuator) to vent the inflatable bladder to the atmosphere so that the bladder may be deflated.

16 Claims, 2 Drawing Figures

MANUALLY-ACTUABLE CPR APPARATUS

FIELD OF THE INVENTION

This invention generally relates to apparatus for effecting cardiopulmonary resuscitation (CPR), and more particularly, to such an apparatus which is manually-actuable and which provides more efficient CPR than currently-used manual CPR techniques.

BACKGROUND OF THE INVENTION

In recent years, manual cardiopulmonary resuscitation (CPR) techniques for reproducing the cardiac and pulmonary functions of a patient have been taught to and used by paramedics, emergency medical technicians, and the general public. Although manual CPR techniques differ somewhat, a typical technique that is designed for use by a single person comprises the following steps. The person first clears the patient's airway (e.g., the mouth, larynx, and the trachea), by removing any obstructions therein, and by tilting the patient's head back and by elevating the patient's chin. After the airway has been cleared, the person reproduces the pulmonary function by breathing into the patient's mouth to inflate the patient's lungs through the airway. The person then reproduces the cardiac function by compressing the patient's chest immediately above the sternum at a predetermined rate, e.g., 80 compressions per minute, in order to compress the patient's heart so as to force blood through the patient's circulatory system. Since a single person cannot both compress the patient's chest and breathe into the patient's mouth at the same time, the technique involves repetitive cycles of a predetermined number of chest compressions, e.g., fifteen, followed by a predetermined number of breaths into the mouth, e.g., two.

Although manual CPR techniques have saved countless lives, they are subject to the disadvantage that they must be used by a person who has been trained in these techniques. In order to have any chance of restoring the patient to normal health, CPR must be started within a certain period of time after the paitent has been stricken. Accordingly, if a trained person is not readily available, the patient will most likely die. Another disadvantage of manual CPR techniques is that they are relatively inefficient in reproducing the cardiac and pulmonary functions. For example, manual CPR techniques can at best result in only a small percentage of the normal blood flow to the patient's brain and only a small percentage of the normal oxygenation of the patient's blood through lung inflation.

The efficiency of CPR may be increased by the used of automated CPR apparatus, sometimes referred to as resuscitators. Although the structure and operation of resuscitators differ, they typically include a reciprocable chest plunger that is positioned by an appropriate mounting frame above the patient's chest or that is secured to the patient's chest by a plurality of straps, and an airway apparatus including a mouth piece which is inserted into the patient's mouth. An appropriate driving means causes the reciprocable chest plunger to be extended to and from the patient's chest so as to compress the heart, and a pressurized air or oxygen source is coupled to the airway apparatus so as to inflate the patient's lungs. Typically, the apparatus is operated in a cyclical mode, each cycle including a plurality of successive chest compressions (e.g., five) followed by a single airway pressurization.

Such automated CPR apparatus are bulky and heavy, and therefore not easily transportable. They also require an external source of power (such as a source of compressed oxygen), and are difficult to use by all but highly-trained paramedics and emergency medical technicians. Therefore, despite their increased efficiency, such automated CPR apparatus generally are not available for use, or are used, by the general public.

Recently, it has been discovered that the mechanism for causing blood to flow through the circulatory system during CPR may not be the force that is transmitted to the heart through the chest during each chest compression, as previously thought, but rather the amount of intrathoracic pressure that is generated in that portion of the thorax in which the heart and lungs are located. It therefore has been postulated that an increase in intrathoracic pressure during CPR should increase the efficiency of CPR. Reference, for example, Rudikoff et al., *Mechanisms Of Blood Flow During Cardiopulmonary Resuscitation,* CIRCULATION, v. 61, No. 2, pp. 345–352 (1980). However, no practical manual CPR apparatus has yet been devised which utilizes this discovery to accordingly increase the intrathoracic pressure of the patient during CPR.

It is therefore an object of this invention to provide a manually-actuable CPR apparatus.

It is another object of this invention to provide such an apparatus which operates by increasing the intrathoracic pressure of the patient.

It is yet another object of this invention to provide such an apparatus which provides more efficient CPR than currently-used manual CPR techniques.

It is a further object of this invention to provide such an apparatus which is small in size and light in weight, and therefore easily transportable, which requires no external source of power other than that provided by the user, which is constructed from ready-available components, and which is easy to use by relatively unskilled persons.

SUMMARY OF THE INVENTION

The foregoing objects, and other objects and advantages that will be recognized after a consideration of the following portion of the specification, are achieved in a manually-actuable apparatus for performing cardiopulmonary resuscitation on a patient by alternately increasing and decreasing the patient's intrathoracic pressure. The apparatus includes:

a manually-actuable bellows adapted to be placed during use on the patient's chest, the bellows including a port means and being capable of being alternately compressed and decompressed so as to alternately pressurize and depressurize said port means and so as to alternately apply force to and remove force from the patient's chest;

an airway apparatus adapted to be placed during use in proximity to the patient's airway so as to couple gas to and from the patient's lungs; and, first means for providing a fluid flow path between the port means of the bellows, the airway apparatus, and a source of gas at atmospheric pressure, the first means including a first valve apparatus which is operative to couple gas from the bellows to the airway apparatus as the port means of the bellows is pressurized during bellows compression, to limit the pressure in the patient's lungs to a desired pressure value during bellows compression, and to couple gas from the patient's lungs and from the source of gas at atmospheric pressure to the bellows as the port means of the bellows is depressurized during bellows decompression.

In the preferred embodiment, the first valve apparatus is located in proximity to and coupled with the airway apparatus (and in fact is integral with the airway apparatus), and the first means also includes a flexible conduit connecting the port means of the bellows to the first valve apparatus.

In use, the CPR apparatus accordingly functions to pressurize the patient's lungs at the same time that the patient's chest is being compressed by force transmitted through the bellows, thereby increasing the patient's intrathoracic pressure so that blood is forced through the circulatory system and oxygenated as the blood passes through the lungs. During bellows decompression, intrathoracic pressure decreases due to removal of force from the patient's chest and to depressurization of the bellows, whereby the heart and lungs refills with blood from the circulatory system and the lungs deflate.

In order that the intrathoracic pressure may be further increased, the CPR apparatus may also comprise:
an abdominal restraint adapted to be secured during use about the portion of the patient's body in the region of the abdomen, the abdominal restraint including an inflatable bladder; and,
second means for providing a fluid flow path between the port means of the bellows and the inflatable bladder, the second means including a second valve apparatus which is operative to pressurize the inflatable bladder as the port means of the bellows is pressurized during bellows decompression.

The second valve apparatus may also be selectively actuable, e.g., by the use of a manual actuator, so as to vent the inflatable bladder to the atmosphere, whereby the inflatable bladder may be deflated.

In the preferred embodiment, the second valve apparatus is located in proximity to the bellows and coupled with the port means thereof, and the second means also includes a flexible conduit connecting the second valve apparatus to the inflatable bladder.

The CPR apparatus is relatively easy to use by any person, since all that is required is that the bellows, the airway apparatus and the abdominal restraint be installed and that the bellows be firmly compressed and decompressed at a desired rate. Each valve apparatus may be constructed from readily-available valves and the entire apparatus is relatively compact and may be fabricated from relatively inexpensive, lightweight plastic materials, so that the apparatus is easily transportable and readily available (because of low cost) to large segments of the public.

BRIEF DESCRIPTION OF THE DRAWINGS

The invention can best be understood by reference to the following portion of the specification, taken in conjunction with the accompanying drawings in which.

DESCRIPTION OF THE PREFERRED EMBODIMENT

Figure 1:
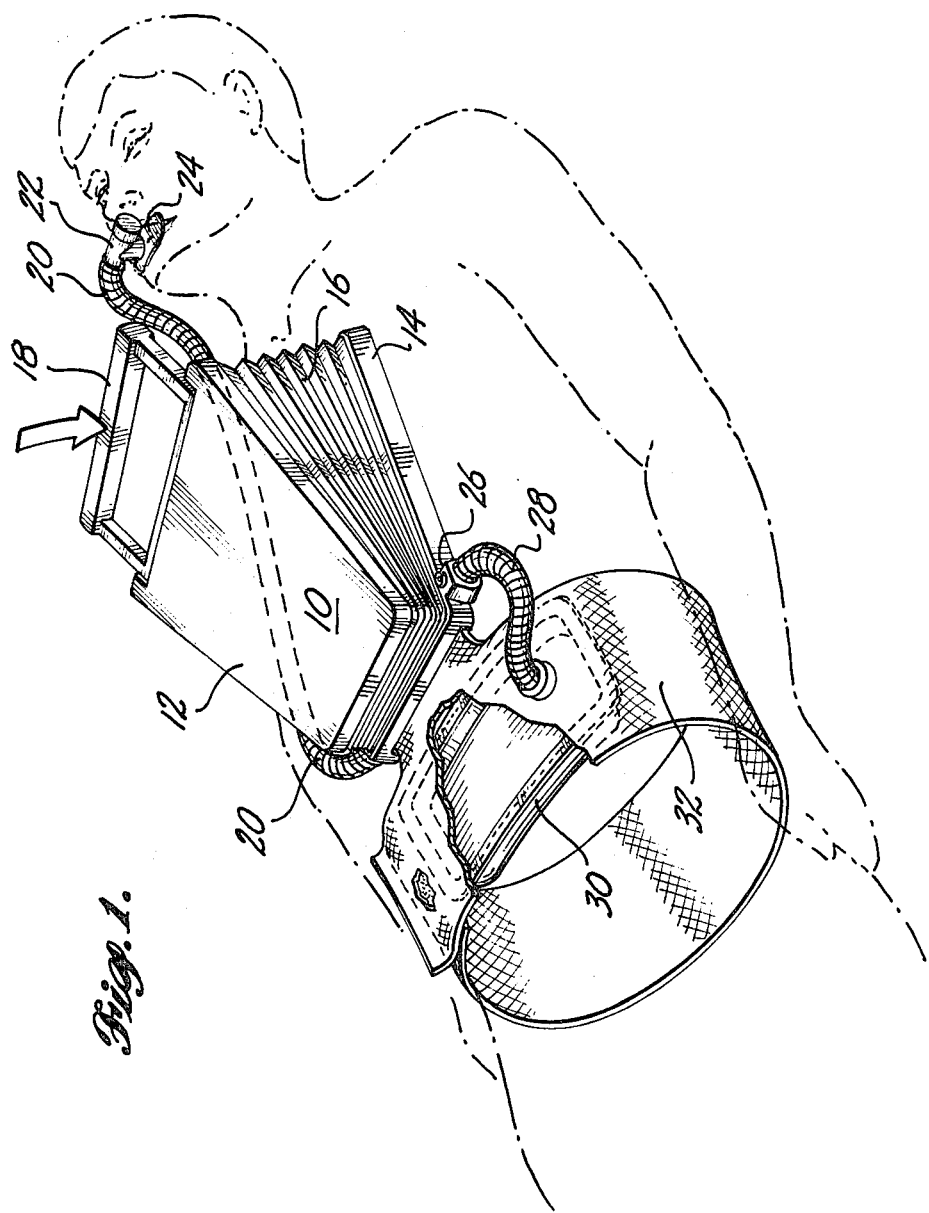
FIG. 1 is a pictorial illustration of the preferred embodiment of the manually-actuable CPR apparatus; and, FIG. 2 is a fluid schematic diagram of the preferred embodiment.

With reference to FIG. 1, the manually-actuable CPR apparatus includes a bellows 10 including a substantially rigid, top plate 12 and a substantially rigid, bottom plate 14 which are joined by a flexible, pleated member 16. Plates 12 and 14 and member 16 define a closed chamber and are maintained in the rest position illustrated in FIG. 1 by an internal spring, not illustrated. In use, bellows 10 is placed on the chest of the patient with bottom plate 14 overlying the patient's rib cage. A handle 18 is integrally formed with top plate 12 and permits the user to compress bellows 10 by grasping handle 18 and applying a downward force thereto. Bellows 10 also includes first and second ports, preferably formed in bottom plate 14, that communicate with the closed chamber within bellows 10 and that permit gas within the closed chamber to be exhausted therefrom upon bellows compression and to be drawn therein upon bellows decompression (when handle 18 is released and the internal spring within bellows 10 returns plates 12 and 14 and member 16 to the rest position illustrated in FIG. 1). The first port is coupled by a flexible conduit 20 to a valve apparatus 22 which in turn is coupled to and integral with an airway apparatus 24 comprising, for example, a mouth piece, a mask, an endotracheal tube, or the like. The second port is coupled through a valve apparatus 26 to a flexible conduit 28 which in turn is connected to an inflatable bladder 30 forming part of an abdominal restraint 32 comprising a flat belt which is secured about the portion of the patient's body in the region of the abdomen by appropriate fastening means, not illustrated (such as Velcro TM fasteners). For convenience, the belt of abdominal restraint 32 is preferably attached to bottom plate 14 of bellows 10, so that the entire CPR apparatus may be transported as a unit.

In use, bellows 10 is compressed and decompressed at a desired rate by the user. For each compression of bellows 10, the force applied by the user to handle 18 is transmitted through bellows 10, and specifically bottom plate 14, to the chest of the patient, thereby compressing the intrathoracic cavity, and the gas within bellows 10 is forced into the patient's lungs through conduit 20, valve apparatus 22 and airway apparatus 24, thereby inflating the lungs. Accordingly, each compression of bellows 10 results in an increase in intrathoracic pressure so that blood is forced through the circulatory system. In addition, the gas that is forced into the lungs results in oxygenation of the blood as the blood passes through the lungs, provided that the gas contains or consists of oxygen. During each compression of bellows 10, valve apparatus 22 functions to limit the pressure that is applied to the lungs to a value that will result in a desired intrathoracic pressure.

The intrathoracic pressure is further increased by the use of abdominal restraint 32. Specifically, valve apparatus 26 functions to pressurize, and thereby inflate, bladder 30 during a compression of bellows 10. Bladder 30 remains inflated during successive compressions of bellows 10, and when so inflated, further increases intrathoracic pressure by limiting the downward deflection of the patient's diaphragm, or, the lower wall defining the intrathoracic cavity.

When the user releases handle 18, the internal spring within bellows 10 returns bellows 10 to its rest position. Since force has been removed from handle 18, the patient's lungs deflate and some of the gas therefrom is coupled back to the closed chamber within bellows 10 through airway apparatus 24, valve apparatus 22, and conduit 20. As bellows 10 is being decompressed, valve apparatus 22 also functions to couple fresh air from the atmosphere (or a gas containing or consisting of oxygen from another atmospheric pressure source thereof, not illustrated) to the closed chamber within bellows 10 through conduit 20, so that the closed chamber within bellows 10 may be completely refilled with gas at the time that bellows 10 has returned to its rest position. The cycle of bellows compression and decompression may then be repeated at any desired rate. When CPR has been completed, or at any other time, valve apparatus 26 may be manually actuated by the user to vent bladder 30 to the atmosphere through conduit 28 and valve apparatus 26, in order to deflate bladder 30.

It will be appreciated that, in order to use the manually-actuable CPR apparatus in FIG. 1, all that is required is that bellows 10 be placed on the patient's chest, that airway apparatus 24 be inserted into the patient's airway, that abdominal restraint 32 be secured about that portion of the patient's body in the region of the abdomen, and that manual force be applied to handle 18 at a desired rate. Simple instructions may be located on bellows 10, so that the manually-actuable CPR apparatus is relatively easy to use by any person. Further, the apparatus is relatively compact and may be fabricated from relatively inexpensive, lightweight plastic materials, so that the apparatus is easily transportable, and readily available (because of low cost) to large segments of the public.

Figure 2:
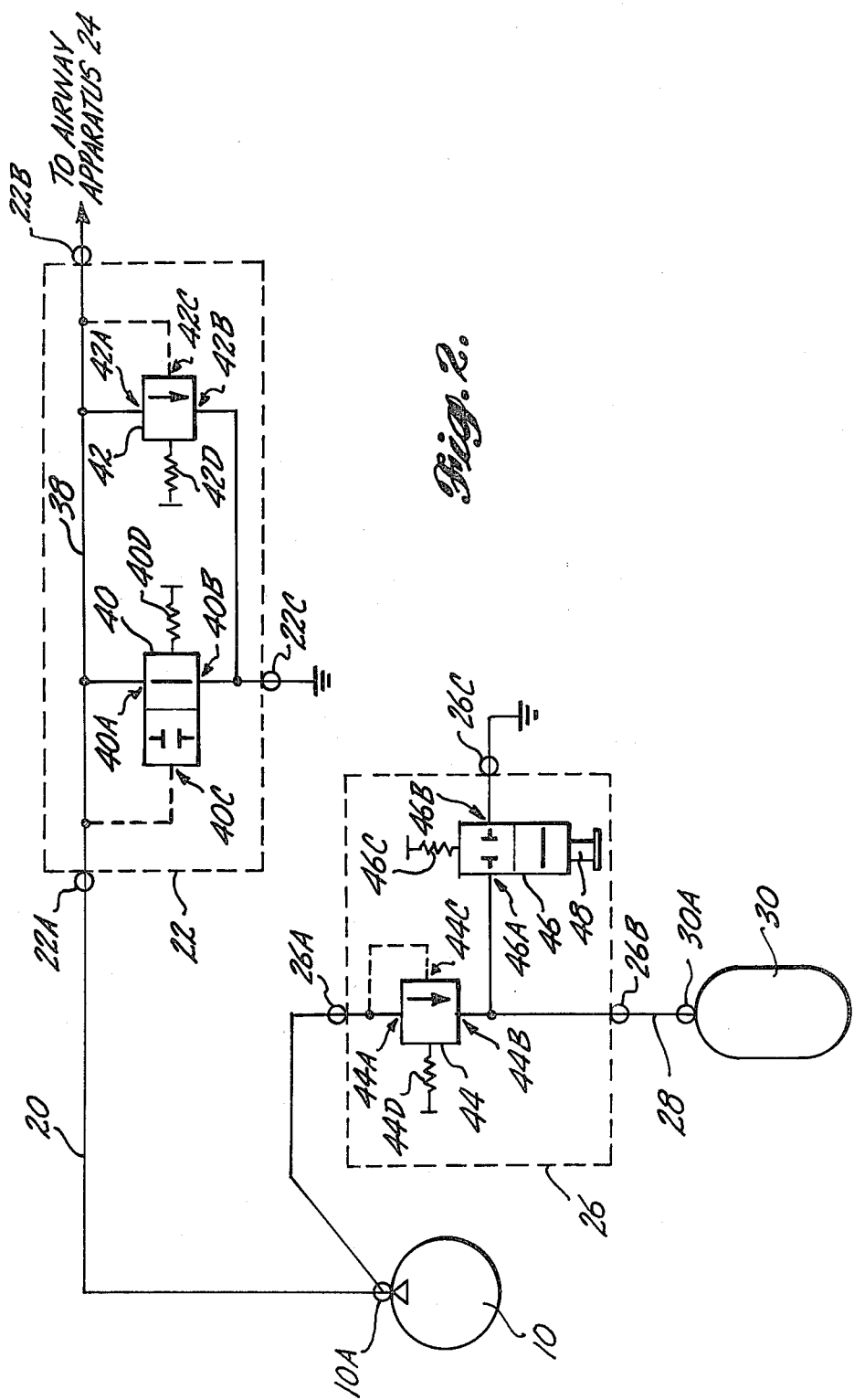

Considering also now the fluid schematic diagram in FIG. 2, the first and second ports of bellows 10 may be considered as a single port 10A which is coupled by conduit 20 to a port 22A of valve apparatus 22 and directly to a port 26A of valve apparatus 26. Valve apparatus 22 also has a port 22B which is coupled to airway apparatus 24, and a port 22C which is coupled to the atmosphere. Valve apparatus 26 also has a port 26B which is coupled by conduit 28 to a port 30A of bladder 30, and a port 26C which is coupled to the atmosphere.

Valve apparatus 22 includes a fluid passageway 38 coupling ports 22A and 22B, a two-position, two-way, pressure-actuated valve 40, and a pressure relief valve 42. First ports 40A, 42A of valves 40, 42 are each coupled to passageway 38, and second ports 40B, 42B of valves 40, 42 are each coupled to port 22C. In addition, control ports 40C, 42C of valves 40, 42 are coupled to passageway 38 at locations adjacent ports 22A, 22B.

As symbolized in FIG. 2, valve 40 is normally open and accordingly provides a fluid flow path between ports 40A, 40B thereof. Whenever the pressure at control port 40C exceeds a predetermined value, as established by an internal spring 40D, valve 40 closes to accordingly block fluid flow between ports 40A and 40B. Valve 42 is normally closed and accordingly blocks fluid flow between ports 42A, 42B thereof. When the pressure at control port 42C exceeds a predetermined value, as established by an internal spring 42D, valve 42 opens to provide fluid flow from port 42A to port 42B (but not in the reverse direction).

Valve apparatus 26 includes a pressure relief valve 44 and a two-position, two-way, manually-actuated valve 46. A first port 44A and a control port 44C of valve 44 are coupled to port 26A, and a second port 44B of valve 44 is coupled both to port 26B and to a first port 46A of valve 46. A second port 46B of valve 46 is coupled to port 26C, and valve 46 also includes a manually-actuable pushbutton 48.

Valve 44 is normally closed and accordingly blocks fluid flow between ports 44A, 44B thereof. When the pressure at control port 44C exceeds a predetermined value, as established by an internal spring 44D, valve 44 opens to couple fluid from port 44A to port 44B (but not in the reverse direction). Valve 46 is normally closed and accordingly blocks fluid flow between port 46A and port 46B thereof. When pushbutton 48 is actuated against the force of an internal spring 46C, valve 46 opens to couple port 46A to port 46B thereof.

To consider the operation of the apparatus in FIGS. 1 and 2 in detail, let it be assumed that the apparatus is in place and that bellows 10 is in its rest position. At this time, it will be appreciated from the following description that bellows 10 is completely filled with gas, that valve 40 is open and valve 42 is closed, and that the pressures within bellows 10, conduit 20, passageway 38 and airway apparatus 24 are all at atmospheric pressure (due to the fluid path through valve 40 to port 22C). As bellows 10 is thereafter compressed, the gas within bellows 10 is forced out through port 10A, conduit 20 and into port 22A and the pressure at port 22A accordingly rises. Since valve 40 is open, this gas is largely vented to the atmosphere through passageway 38, valve 40, and port 22C. Further compression of bellows 10 causes the pressure at port 22A to continue to rise until the pressure at port 22A exceeds the predetermined value of pressure required to close valve 40 (which may be a small pressure above atmospheric pressure). At this time, valve 40 closes and the gas within bellows 10 is coupled to the airway apparatus through passageway 38 and port 22B, with a consequent rise in pressure throughout passageway 38 and at port 22B. Upon further compression of bellows 10, the gas therefrom inflates the patient's lungs until the pressure of the gas going into the patient's lungs (e.g., that at port 22B) exceeds the predetermined value of pressure required to open valve 42. At this time, valve 42 opens and remains open upon further compression of bellows 10 so as to vent the remaining gas in bellows 10 to the atmosphere through port 22C and to maintain the pressure in the patient's lung at a constant value, e.g., the value of pressure required to open valve 42.

The intrathoracic pressure that must be generated by the apparatus is preferably in the range of arterial blood pressures for a normally-functioning heart, e.g., 50–200 mm Hg. Accordingly, the predetermined value that is required to open valve 42, and therefore the pressure that is maintained within the lungs upon each bellows compression, is also within this range, and a value of 88 mm Hg has been found to work well. It will be recognized, however, that intrathoracic pressure is also generated by the application of force to the patient's chest through bellows 10, and may also vary depending on whether or not abdominal restraint 32 is used. Those skilled in the art will accordingly recognize that the predetermined value of pressure that is required to open valve 42 may be empirically varied to fit a specific design and operating mode of the apparatus.

When bellows 10 has been fully compressed and handle 18 has been released by the user, bellows 10 begins to return to its rest position. At this time, the pressure at port 10A, and therefore the pressures within conduit 20 and at port 22A, rapidly drop and go to a negative pressure below atmospheric pressure. As the pressure at port 22A drops, the pressure within passageway 38 and therefore the pressure at port 22B also drops, so that valve 42 closes. When the pressure at port 22A passes through the predetermined value of pressure established by spring 40D, valve 40 opens. As bellows 10 thereafter expands and returns to its rest position, the patient's lungs deflate and bellows 10 is refilled with some of the gas that it expelled from the patient's lungs upon deflation (through port 22B, passageway 38, port 22A and conduit 20) and with air from the atmosphere (through port 22C, valve 40, passageway 38, port 22A, and conduit 20).

Let it now be assumed that bladder 30 of abdominal restraint 32 is deflated, e.g., is at atmospheric pressure, and that bellows 10 is being compressed for the first time. The consequent rise in pressure at port 10A of bellows 10, and therefore at port 26A of valve apparatus 26, causes valve 44 to open (the predetermined value of pressure required to open valve 44 is very small), whereby gas from bellows 10 is coupled through valve 44 and into bladder 30. During each compression of bellows 10, valve 44 opens so as to fully inflate bladder 30. However, valve 44 closes during each decompression of bellows 10 so as to maintain bladder 30 fully inflated. To deflate bladder 30, pushbutton 48 is actuated by the user so that the gas within bladder 30 is vented to the atmosphere through conduit 28, port 26B, valve 46, and port 26C.

While the invention has been described with reference to a preferred embodiment, it is to be clearly understood by those skilled in the art that the invention is not limited thereto. Rather, the scope of the invention is to be interpreted only in conjunction with the appended claims.

The embodiments of the invention in which an exclusive property or privilege is claimed are defined as follows:

1. A manually-actuable apparatus for performing cardiopulmonary resuscitation on a patient by alternately increasing and decreasing the patient's intrathoracic pressure, said apparatus comprising:
   a manually-actuable bellows including means adapted to be placed during use on the patient's chest, said bellows including a port means and being capable of being alternately compressed and decompressed so as to alternately pressurize and depressurize said port means and so as to alternately apply force to and remove force from the patient's chest;
   an airway apparatus including means adapted to be placed during use in proximity to the patient's airway so as to couple gas to and from the patient's lungs; and,
   first means for providing a fluid flow path between said port means of said bellows, said airway apparatus, and a source of gas at atmospheric pressure, said first means including a first valve apparatus which is operative to limit the pressure in the patient's lungs to a desired pressure value as said port means of said bellows is pressurized during bellows compression and which is further operative to couple gas from the patient's lungs and from the source of gas at atmospheric pressure to said bellows as said port means of said bellows is depressurized during bellows decompression.

2. An apparatus as recited in claim 1, wherein said first valve apparatus is located in proximity to and coupled with said airway apparatus, and wherein said first means also includes a flexible conduit connecting said port means of said bellows with said first valve apparatus.

3. An apparatus as recited in claim 1, wherein said bellows includes: a substantially rigid, top plate, and a handle integral with said top plate; a substantially rigid, bottom plate adapted to rest on the patient's chest; and, a flexible, pleated member joining said top plate and said bottom plate so as to define a closed chamber which communicates with said port means, said bellows being operative to pressurize said port means by expelling gas from said closed chamber and to apply force to the patient's chest as said bellows is compressed by the application of manual force to said handle, said bellows being further operative to depressurize said port means whereby said closed chamber may be filled with gas through said port means and to remove force from the patient's chest as said bellows is decompressed by removal of manual force from said handle.

4. An apparatus as recited in claim 1, wherein said first valve apparatus includes: first, second, and third ports respectively coupled to said port means of said bellows, to said airway apparatus, and to the atmosphere; a passageway providing a fluid flow path between said first and said second ports; a first valve for providing a bidirectional fluid flow path between said passageway and said third port, said bidirectional fluid flow path being normally opened and being closed whenever the pressure at said first port exceeds a first predetermined value greater than atmospheric pressure; and, a second valve for providing a unidirectional fluid flow path from said passageway to said third port, said unidirectional fluid flow path being normally closed and being opened whenever the pressure at said second port exceeds a second predetermined value which is greater than said first predetermined value and which is substantially equal to said desired pressure value.

5. An apparatus as recited in claim 4, wherein said first valve is a two-position, two-way pressure-actuated valve.

6. An apparatus as recited in claim 4, wherein said second valve is a pressure relief valve.

7. An apparatus as recited in claim 1, wherein said desired pressure value is in the range of 50–200 mm Hg.

8. An apparatus as recited in claim 7, wherein said desired pressure value is substantially 88 mm Hg.

9. An apparatus as recited in claim 1, further comprising: an abdominal restraint adapted to be secured during use about the portion of the patient's body in the region of the abdomen, said abdominal restraint including an inflatable bladder; and, a second means for providing a fluid flow path between said port means of said bellows and said inflatable bladder, said second means including a second valve apparatus which is operative to pressurize said inflatable bladder as said port means of said bellows is pressurized during bellows compression.

10. An apparatus as recited in claim 9, wherein said second valve apparatus is selectively actuable to vent said inflatable bladder to the atmosphere.

11. An apparatus as recited in claim 10, wherein said second valve apparatus includes: first, second and third ports respectively coupled to said port means of said bellows, to said inflatable bladder, and to the atmosphere; a first valve for providing a unidirectional fluid flow path from said first port to said second port, said unidirectional fluid flow path being normally closed and being opened whenever the pressure at said first port exceeds a first predetermined value greater than atmospheric pressure; and, a second valve including a manual actuator for providing a bidirectional fluid flow path between said first port and said third port, said bidirectional fluid flow path being normally closed and being opened whenever said second valve is being manually actuated.

12. An apparatus as recited in claim 11, wherein said first valve is a pressure relief valve.

13. An apparatus as recited in claim 11, wherein said second valve is a two-position, two-way manually-actuated valve.

14. An apparatus as recited in claim 9, wherein said second valve apparatus is located in proximity to said bellows and coupled with said port means thereof, and wherein said second means also includes a flexible conduit connecting said second valve apparatus to said inflatable bladder.

15. An apparatus as recited in claim 9, further comprising means for mechanically attaching said abdominal restraint to said bellows.

16. An apparatus as recited in claim 1, further comprising an abdominal restraint that is integral with said bellows and that is adapted to be secured during use about the portion of the patient's body in the region of the abdomen so as to further increase the patient's intrathoracic pressure as said bellows is compressed.

* * * * *